(12) United States Patent
Krueger

(10) Patent No.: US 6,616,647 B1
(45) Date of Patent: Sep. 9, 2003

(54) MACHINE DIRECTION MANUFACTURED PANT

(75) Inventor: Gary A. Krueger, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/604,750

(22) Filed: Jun. 27, 2000

(51) Int. Cl.[7] .......................... A61F 13/20; A61F 13/15; A41B 9/00
(52) U.S. Cl. ...................... 604/385.23; 604/385.01; 604/385.29; 604/392; 604/396; 2/400
(58) Field of Search ............ 604/385.01, 385.21–385.3, 604/392–396; 2/400–408

(56) References Cited

U.S. PATENT DOCUMENTS

| | | | |
|---|---|---|---|
| 4,205,679 A | * | 6/1980 | Repke et al. ................. 604/366 |
| 4,319,572 A | * | 3/1982 | Widlund et al. ......... 604/385.24 |
| 4,336,803 A | * | 6/1982 | Repke .................... 604/385.25 |
| 4,695,278 A | * | 9/1987 | Lawson .................. 604/385.28 |
| 4,771,483 A | * | 9/1988 | Hooreman et al. .......... 604/392 |
| 4,822,435 A | * | 4/1989 | Igaue et al. ............. 604/385.28 |
| 4,906,243 A | * | 3/1990 | Dravland .................... 604/394 |
| 5,074,854 A | | 12/1991 | Davis |
| 5,147,487 A | | 9/1992 | Nomura et al. |
| 5,382,246 A | * | 1/1995 | Kawano ................. 604/385.24 |
| 5,389,173 A | | 2/1995 | Merkatoris et al. |
| 5,545,158 A | | 8/1996 | Jessup |
| 5,735,840 A | * | 4/1998 | Kline et al. ............. 604/385.23 |
| 6,102,900 A | * | 8/2000 | Roessler et al. ............. 604/343 |
| 6,260,211 B1 | * | 7/2001 | Rajala et al. ........... 604/385.21 |
| 6,393,621 B1 | * | 5/2002 | Redwine et al. ................ 2/406 |
| 2002/0052591 A1 | * | 5/2002 | Zehner et al. .......... 604/385.01 |

FOREIGN PATENT DOCUMENTS

| | | | |
|---|---|---|---|
| EP | 349795 A2 | * 1/1990 | ............ A61F/13/15 |
| EP | 630632 A2 | * 12/1994 | ............ A61F/13/15 |
| JP | 3-107919 | * 11/1991 | |
| JP | 4-109943 | * 4/1992 | |
| JP | 9290003 A1 | * 11/1997 | |
| WO | WO 8907923 A1 | * 9/1989 | ............ A61F/13/16 |
| WO | 94/09736 | 5/1994 | |

* cited by examiner

*Primary Examiner*—Karin M Reichle
(74) *Attorney, Agent, or Firm*—Pauley Petersen Kinne & Erickson

(57) ABSTRACT

An undergarment is conveniently made with two elasticized top panels bonded and cut at a 45 degree angle on a bottom panel. The top panels have curved leg cutouts matched to the curved leg cutouts of the bottom panel. The curved leg cutouts are preferentially cut for the front and back sections of the garment to produce a comfortable fit.

12 Claims, 2 Drawing Sheets

MACHINE DIRECTION MANUFACTURED PANT

BACKGROUND OF THE INVENTION

1. Field of the Invention

The present invention relates generally to undergarments made from webs of nonwoven material. The present invention relates more specifically to undergarments made from webs of nonwoven material which are fastened in opposing relation and fused to form various panel areas of the completed undergarment.

2. Discussion of the Related Art

Undergarments made from webs of nonwoven material are well known, especially in the area of diapers, training pants and the like. Some of these undergarments are known to place two elasticized panels on top of, or in opposition to, a bottom panel. The top panels and the bottom panel are then secured together with four forty five degree end bonds resulting in an undergarment which is openable to have the top panels serve primarily as waist band areas, while the bottom panel serves primarily as the crotch and front and back panels of the undergarment. Such garments, with the addition of suitable layers such as at least a hydrophobic outer covering and an absorbent panel, may serve as incontinence garments.

However, in the past the garments have not performed satisfactorily owing to lack of comfort to the wearer resulting from the generally rectangular shape of each panel used to construct the undergarment.

SUMMARY OF THE INVENTION

It is therefore desirable to address this short-coming in the art by producing an undergarment having the ease of manufacture of typical nonwoven undergarments, but comfort more like that of a fitted undergarment of traditional sewn cloth.

The present invention addresses this need by providing an undergarment having a bottom panel from a first web cut to have left and right curved leg cutouts. Top right and left panels from a second web and a third web, respectively, each with a curved leg cutout are superimposed on the bottom panel web and joined to the bottom panel with seams at angles to the longitudinal axis of the webs. The leg cutouts of one embodiment are further shaped with a compound curve to delineate the front and back of the undergarment and provide further comfort, or protection, or both to the wearer. Other embodiments may have at least the bottom panel constructed of layers useful for an incontinence undergarment.

The foregoing and other features and advantages of the invention will become further apparent from the following detailed description of the presently preferred embodiments, read in conjunction with the examples and drawings. The detailed description, examples and drawings are merely illustrative rather than limiting, the scope of the invention being defined by the appended claims and equivalents thereof.

DETAILED DESCRIPTION OF THE PRESENTLY PREFERRED EMBODIMENTS

Figure 1:
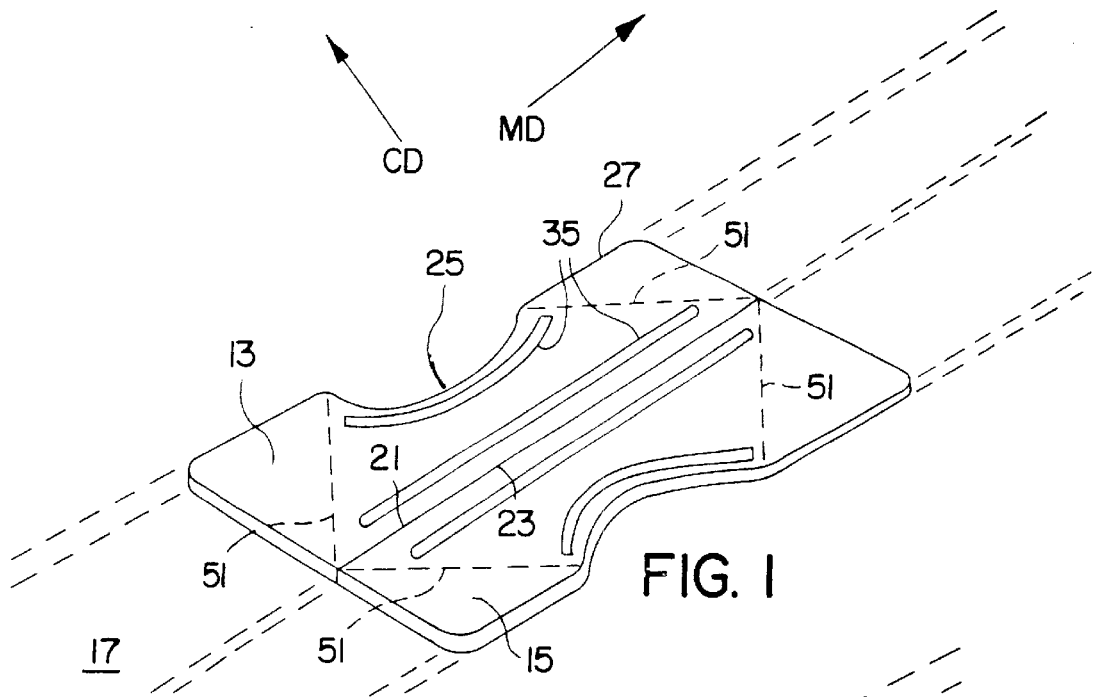
FIG. 1 is a perspective view of the top right panel and top left panel.

Referring to FIG. 1, a top left panel 13 and top right panel 15 are indicated within their respective first and second webs (indicated at 17, 19 in phantom) which may be separately manufactured or created from centrally cutting a precursor web, etc. The first and second webs 17, 19 are closely held together along one inside longitudinal margin 21, 23, respectively, thereof. As the top right and top left panels are mirror images of one another, hereinafter only one will be described. The top left panel 13 has a curved leg cutout 25 on its outside longitudinal margin 27. It will be noted that while the preferred embodiment is set forth as made with the longitudinal axes of the panels in the machine direction (direction of web travel), the ordinarily skilled artisan in the field of nonwoven undergarment manufacturing will recognize that with adaptation, the longitudinal axes of the panels may be in the cross machine, or cross, direction.

Figure 3:
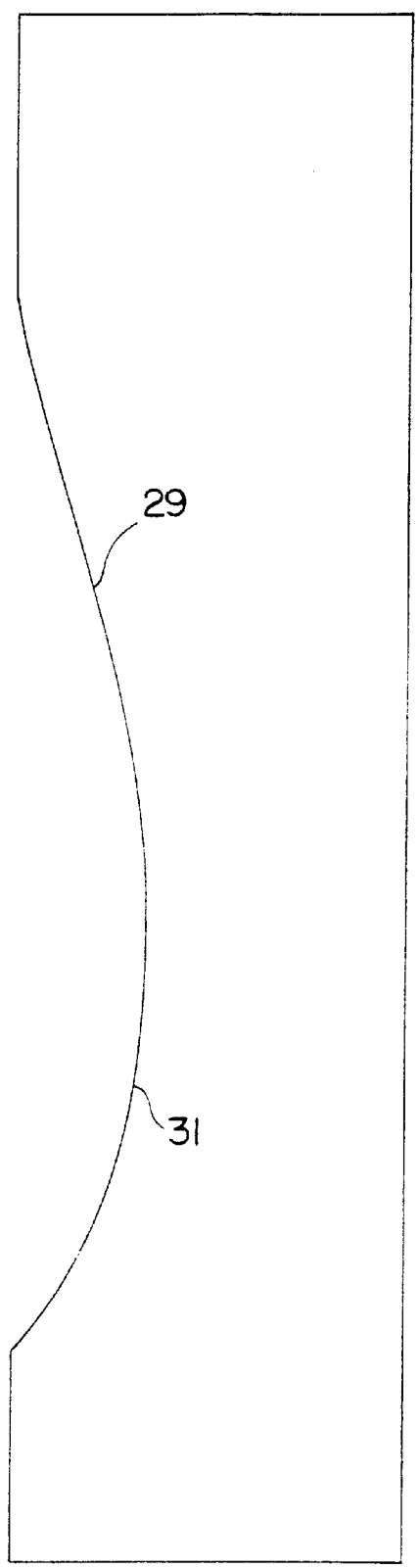
FIG. 3 is a schematic top plan view of one top panel illustrating the compound curve leg cutout.
Figure 4:
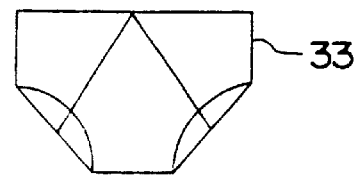
FIG. 4 is a front elevation of a completed undergarment.

The curved leg cutout 25, as best seen in FIG. 3, is, in one embodiment, a compound curve having a first shallow, or large-radiused curved portion 29 and a second curved portion 31 with a lesser radius of curvature. The shallow curve corresponds to the wider back panel, or buttocks-covering area, of the assembled garment 33 (FIG. 4). The steep curve corresponds to the narrower front panel, or pubic-covering area, of the assembled garment. By this means, a more natural fit and greater comfort is obtained for the wearer of the garment.

If desired, the top panels may be made from a material that is itself highly elastic, i.e., with a modulus of elasticity favorable for making the garment adhere closely to the flesh of the wearer. Alternatively, or in addition, elastic strips, collectively 35, may be placed at the margins of the leg cutout 25 and the inside longitudinal margin 21 which will later serve as a waist area, or band, of the garment 33, as further explained below.

Figure 2:
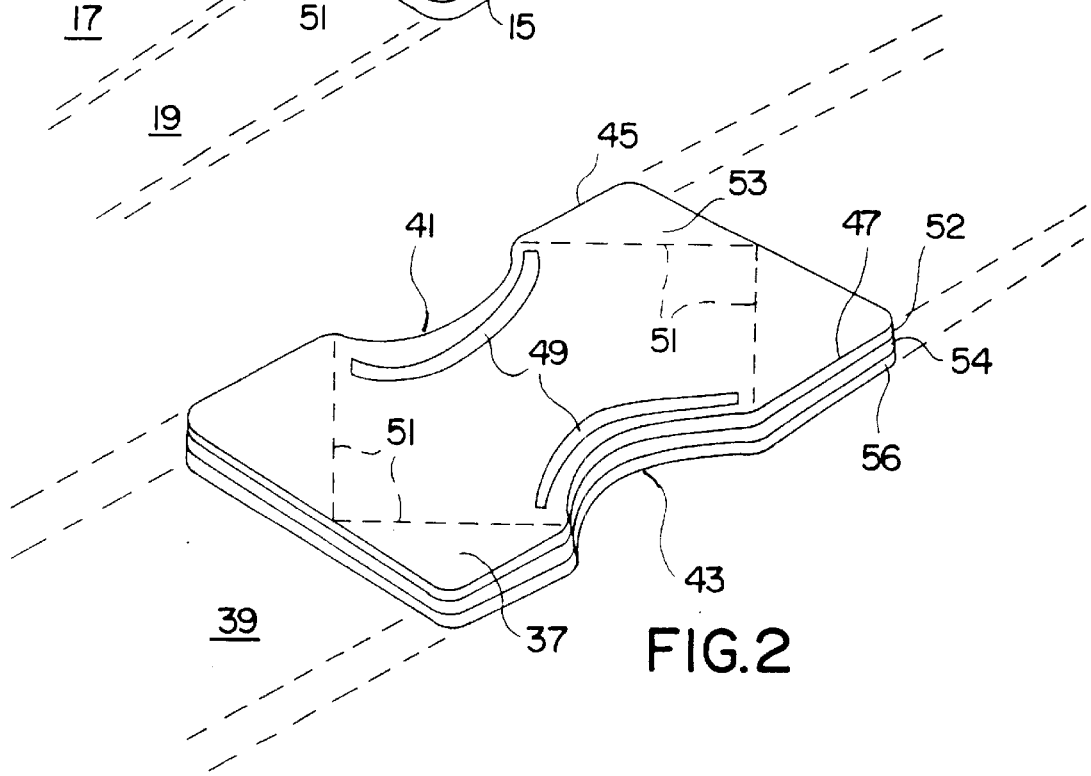
FIG. 2 is a perspective view of the bottom panel.

Referencing FIG. 2, a bottom panel 37 is indicated within its web 39, respectively here the third web. The bottom panel 37 has a left leg cutout 41 and a right leg cutout 43, from the perspective of FIG. 2. Each bottom panel leg cutout 41, 43 is curved, preferably matching the corresponding top panel leg cut curve, as described above, and is centrally located on an outside longitudinal margin 45, 47 of the bottom panel 37. The bottom panel 37 may have elastic strips 49 at the margins of each leg cutout 41,43. The bottom panel has little need for waist elastics since it will not form a majority of the waistband of the finished garment 33. The bottom may be created in the manner of a diaper or other incontinence garment with a smooth inner liner layer 52, a medial absorbent layer 54, and a hydrophobic outer cover layer 56. Such construction, as well as the addition of members such as containment flaps, etc., is within the ordinary skill of the art and will not be further elaborated on. The lines of the eventual cut and bond process are indicated by dashed lines, collectively 51, desirably having an angle of forty-five degrees to the longitudinal axis of each panel as well as to its outside longitudinal margin(s).

At the time for making the undergarment 33, the top panels 13, 15 are brought together closely aligned but not overlapping with each other and superimposed in close proximity to the bottom panel 37, desirably with all leg holes and margins of the panels aligned. The top right and left panels 13, 15 and bottom panel 37 are then joined together by thermal ultrasonic bonding or the like, and cut through along forty-five degree lines 51 with the waist corners., e.g., 53, being removed thereafter, as at reference number 55 in FIG. 5, which illustrates an in process view of a garment of the present invention. The completed garment 33 is then separated from the combined web 57 and is ready for subsequent processing, handling, packaging or the like.

Figure 5:
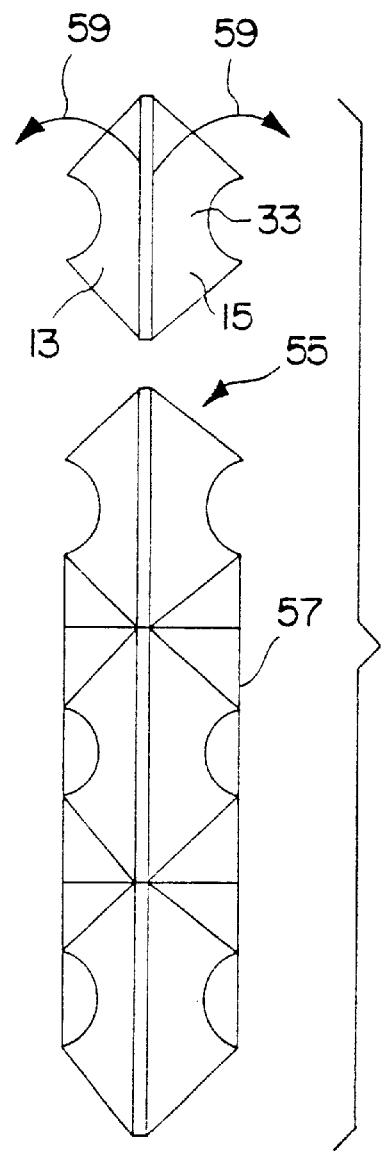
FIG. 5 is a top plan view of in-process formation of the undergarment.

Referring to FIGS. 4 and 5, to place the garment in condition for wearing the user separates the top panels 13, 15 at their inside longitudinal margins by pulling upward and outward in the directions indicated by arrows 59 of FIG. 5 resulting in the garment view as shown in FIG. 4.

While the embodiments disclosed herein are presently considered to be preferred, various modifications and improvements can be made without departing from the spirit and scope of the invention. The scope of the invention is indicated by the appended claims, and all changes that fall within the meaning and range of equivalents are intended to be embraced therein.

I claim:

1. An undergarment of nonwoven fabric comprising:
   a. a bottom panel composed of a first web with a longitudinal axis and having left and right curved leg cutouts;
   b. a top right panel composed of a second web with a longitudinal axis and having a curved leg cutout, the top right panel curved leg cutout being a compound curve with a first shallow radius curved portion and a second curved portion with a lesser radius than the first curved portion;
   c. a top left panel composed of a third web with a longitudinal axis and having a curved leg cutout, the top left panel curved leg cutout being a compound curve with a first shallow radius curved portion and a second curved portion with a lesser radius than the first curved portion; and
   d. the top left panel and the top right panel being superimposed on the bottom panel and joined to the bottom panel with seams at angles to the longitudinal axes of the webs, and
   e. the bottom panel curved leg cutouts each being a compound curve with a first shallow radius curved portion and a second curved portion with a lesser radius than the first curved portion.

2. The undergarment of nonwoven fabric of claim 1 wherein the angle of the seams is 45 degrees.

3. The undergarment of nonwoven fabric of claim 2 wherein the top right and top left panels are made from highly elastic material.

4. The undergarment of nonwoven fabric of claim 2 wherein the top right and left panels have a highly elastic material placed thereon forming leg elastics at margins of the curved leg cutouts.

5. The undergarment of nonwoven fabric of claim 4 wherein the bottom panel comprises an inner liner layer, a medial absorbent layer, and an outer hydrophobic cover layer.

6. The undergarment of nonwoven fabric of claim 5 wherein the bottom panel further has elastic portions at margins of the leg cutouts.

7. The undergarment of nonwoven fabric of claim 6 wherein the leg cutouts of the top panels are aligned at their edges with the leg cutouts of the bottom panel.

8. The undergarment of nonwoven fabric of claim 1 wherein the top right and top left panels are made from a highly elastic material.

9. The undergarment of nonwoven fabric of claim 1 wherein the top right and left panels have a highly elastic material placed thereon forming leg elastics at margins of the curved leg cutouts.

10. The undergarment of nonwoven fabric of claim 1 wherein the bottom panel comprises an inner liner layer, a medial absorbent layer, and an outer hydrophobic cover layer.

11. The undergarment of nonwoven fabric of claim 1 wherein the bottom panel further has elastic portions at margins of the leg cutouts.

12. The undergarment of nonwoven fabric of claim 1 wherein the leg cutouts of the top panels are aligned at their edges with the leg cutouts of the bottom panel.

\* \* \* \* \*